United States Patent
Oguni et al.

(10) Patent No.: US 7,970,200 B2
(45) Date of Patent: *Jun. 28, 2011

(54) PATTERN INSPECTION METHOD AND APPARATUS

(75) Inventors: Teppei Oguni, Kanagawa (JP); Tatsuji Nishijima, Kanagawa (JP); Akiharu Miyanaga, Kanagawa (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/801,793

(22) Filed: Jun. 25, 2010

(65) Prior Publication Data

US 2010/0329541 A1    Dec. 30, 2010

Related U.S. Application Data

(62) Division of application No. 11/334,476, filed on Jan. 19, 2006, now Pat. No. 7,769,226.

(30) Foreign Application Priority Data

Jan. 26, 2005    (JP) ................................ 2005-018004

(51) Int. Cl.
   *G06K 9/00*    (2006.01)
   *H04N 7/18*    (2006.01)
(52) U.S. Cl. ............ 382/145; 382/165; 348/87; 348/126
(58) Field of Classification Search .................. 382/145, 382/165

See application file for complete search history.

(56) References Cited

U.S. PATENT DOCUMENTS

| 5,027,417 | A | * | 6/1991 | Kitakado et al. ............... 382/148 |
| 5,483,603 | A | * | 1/1996 | Luke et al. ..................... 382/147 |
| 6,064,478 | A | * | 5/2000 | Paul et al. ................... 356/237.1 |
| 6,366,688 | B1 | * | 4/2002 | Jun et al. ........................ 382/145 |
| 6,700,658 | B2 | | 3/2004 | Leonard |
| 6,757,428 | B1 | * | 6/2004 | Lin et al. ........................ 382/165 |
| 6,891,967 | B2 | * | 5/2005 | Prince ............................ 382/150 |
| 6,947,151 | B2 | * | 9/2005 | Fujii et al. ...................... 356/612 |
| 6,950,545 | B1 | * | 9/2005 | Nomoto et al. ................. 382/141 |
| 6,963,425 | B1 | * | 11/2005 | Nair et al. ....................... 358/1.9 |
| 6,975,391 | B1 | * | 12/2005 | Asano et al. ................ 356/237.1 |
| 6,975,754 | B2 | * | 12/2005 | Hiroi et al. ..................... 382/149 |
| 2005/0078242 | A1 | | 4/2005 | Park et al. |
| 2007/0237415 | A1 | * | 10/2007 | Cao et al. ....................... 382/254 |

FOREIGN PATENT DOCUMENTS

| JP | 2004-125434 | 4/2004 |
| JP | 2004-163113 | 6/2004 |
| JP | 2004-163115 | 6/2004 |

* cited by examiner

*Primary Examiner* — Kathleen S Yuan
(74) *Attorney, Agent, or Firm* — Nixon Peabody LLP; Jeffrey L. Costellia

(57) ABSTRACT

A color image of an inspection object is taken by an imaging means capable of taking a color image to obtain color information of an RGB color space. A gray-scale image of a color component of the RGB color space or another color space is generated, and the inspection object is detected by a pattern recognition technique. Alternatively, a binary image is generated from the generated gray-scale image, and the inspection object is detected by performing pattern recognition on the binary image. Color data of a pixel occupied by the detected inspection object is compared with color data of a non-defective inspection object which is previously prepared to judge whether or not the inspection object is defective. In addition, this judgment result is reflected in another manufacturing step through a network and product quality is improved.

6 Claims, 7 Drawing Sheets

| Contact hole No. | Avarage of Saturation | Result |
|---|---|---|
| 301 | 138.98 | OK |
| 302 | 209.62 | NG |
| 303 | 68.24 | OK |
| 304 | 68.16 | OK |
| 305 | 71.45 | OK |
| 306 | 216.31 | NG |
| 307 | 145.56 | OK |

FIG. 6

PATTERN INSPECTION METHOD AND APPARATUS

BACKGROUND OF THE INVENTION

1. Field of the Invention

The present invention relates to a pattern inspection method and a pattern inspection apparatus in conducting an in-process inspection in a manufacturing process.

2. Description of the Related Art

Automation of various kinds of microscopy by image processing has been advanced in a manufacturing process of a semiconductor device. One of microscopes used for inspection is an optical microscope; however, an automated inspection by the optical microscope is limited to the case where an object is a circuit pattern or the like. Automation of optical microscopy of an inspection object which has a finer structure than the circuit pattern or the like has not been advanced so much. It is an actual condition where the optical microscopy is mainly performed visually by an inspector.

Although a digital camera attached to an optical microscope or a laser microscope can take an image of an inspection object as a color image, a monochrome image is often used in image processing after taking an image. However, it is known that a subtle difference among inspection objects, which is difficult to distinguish with a monochrome image, can be distinguished if a color image is used. Reference 1 is an example where a color image is used for an appearance inspection (Reference 1: Japanese Patent Laid-Open No. 2004-125434).

As described above, optical microscopy in a manufacturing process is currently mainly conducted visually by an inspector. However, a visual inspection is also desired to be automated for cost reduction by further improvement in efficiency.

SUMMARY OF THE INVENTION

The present invention is devised in order to solve the above-described problem, and it is an object of the present invention to provide an inspection method and an inspection apparatus which can simply and easily judge an inspection object by taking an image of the inspection object over a substrate, generating data of the taken color image, and performing image processing.

If image processing is performed on a color image, detailed characteristics of an inspection object can also be captured. Therefore, an automation of an inspection of an inspection object, which has not been intended for automation of inspection so far, can be expected.

In Reference 1, a microscope is not used, and a relatively large electronic circuit component is assumed as an inspection object. The electronic circuit component is an object having such a size as to be able to be inspected visually by an inspector.

The following measures are taken in the invention to achieve the above-described object.

The present invention provides a pattern inspection method having the steps of converting first color information including three color coordinate components, red (R), green (G), and blue (B), of an RGB color space obtained from a color image of an inspection surface over a substrate into second color information including three color coordinate components of another color space, and specifying the position of an inspection object and judging the inspection object based on the second color information.

Note that one feature of the invention is that the position of the inspection object is specified based on a characteristic amount of an image obtained using the second color information, the position of the inspection object is specified using a first color coordinate component selected from the second color information, and the inspection object is judged by comparing a second color coordinate component selected from the second color information with preset color data of a non-defective unit (a reference color coordinate component of non-defective reference color information).

Specifically, a color image of an inspection substrate is taken first. In the present invention, a color image, which is taken using a digital camera attached to an optical microscope while a predetermined position of the inspection substrate is irradiated with white light, can be used. Here, an imaging means is not limited to the optical microscope and the digital camera as long as the image means can take a color image. For example, a laser microscope may be used instead of the optical microscope.

The color image is transmitted from the digital camera to a computer and is stored in a memory of the computer. The color image has color information including color coordinate components of an RGB color space (hereinafter referred to as first color information).

In the invention, second color information including color coordinate components of a color space other than the RGB color space (hereinafter referred to as a second color space) is calculated from the first color information of the color image, using a conversion formula, and the second color information is stored in the memory.

Here, the second color space may be any three-dimensional or four-dimensional color space, and is not limited to a specific color space. For example, there is an HSB color space including three color components, hue, saturation, and brightness, or the like as the color space other than the RGB color space. However, since each color space has its own characteristic, a color space which can capture characteristics of the inspection object well may be appropriately selected as the second color space in converting the RGB color space into the second color space.

After calculating the color information of the second color space, one color coordinate component (first color coordinate component) is selected from the color coordinate components of the second color space to generate a gray-scale image expressed by the value of the first color coordinate component. Here, as the first color coordinate component, a color coordinate component which can capture characteristics of the inspection object well may be appropriately selected.

After generating the gray-scale image, image processing such as pattern matching is performed to detect all of the inspection objects included in the gray-scale image. Simultaneously, coordinate data of each pixel occupied by each inspection object is stored in the memory on a per inspection object basis. This makes it possible to specify the position of the inspection object.

The position of the inspection object may be specified not by performing image processing such as pattern matching on the gray-scale image but by generating a binary image from the gray-scale image with a threshold appropriately determined and performing pattern matching or the like on the binary image.

After obtaining the coordinate data of the pixel occupied by the inspection object, another color coordinate component (second color coordinate component) is selected from the color coordinate components of the RGB color space or the second color space to take statistics of the second color coordinate component in the pixel occupied by the inspection object. Here, as the second color coordinate component, a component which distinctly shows whether or not the inspection object is defective may be appropriately selected. Thereafter, the inspection object is judged by comparing the second color coordinate component and a reference color coordinate component of preset non-defective reference color information. Note that the judgment here may be performed by an appropriately-selected method, for example, by comparing histograms.

Note that the above-described conversion from the RGB color space into another color space is not limited to conversion into a single color space, and the RGB color space may be converted into a plurality of color spaces. In other words, the RGB color space may be converted into as many color spaces as needed to capture the characteristics of the inspection object.

In the case where it is not necessary to detect the inspection object by pattern recognition, such as when a color tone/coloration of the entire substrate is intended to be examined, the color information of the second color space may be analyzed without performing pattern recognition. In that case, the gray-scale image may not be generated, if not necessary.

In the invention, the judgment result is transmitted to another computer such as a server through a network, and the judgment result is used as data for judging manufacturing process conditions to determine the manufacturing process conditions. Accordingly, product quality can be improved.

Further, the invention provides a pattern inspection apparatus using the above-described pattern inspection method.

As described above, optical microscopy in a manufacturing process of a semiconductor device is currently mainly conducted visually by an inspector. However, if the pattern inspection method of the invention by image processing is used, an automation of an inspection which has been difficult to automate becomes possible, and labor saving and cost reduction can be expected. In addition, since a color image, which has not so far been used so much in an automated inspection by image processing, is used in the invention, a more detailed inspection than ever before becomes possible. Further, in the invention, the judgment result of inspection is transmitted to another computer through a network, and the judgment result is used as data for judging manufacturing process conditions to determine the manufacturing process conditions. Accordingly, product quality can be improved.

BRIEF DESCRIPTION OF DRAWINGS

The patent or application file contains at least one drawing executed in color. Copies of this patent or patent application publication with color drawings will be provided by the Office upon request and payment of the necessary fee.

FIG. 6 shows a judgment result, whether or not a contact hole is defective, by an inspection method of the present invention.

DETAILED DESCRIPTION OF THE INVENTION

Hereinafter, a method for detecting defective etching of a contact hole in a manufacturing process of a thin film transistor (hereinafter referred to as a TFT) to which the present invention is applied is explained as an embodiment mode of the invention. Since the embodiment mode to be explained hereinafter is one specific example of the invention, various limitations are imposed. However, it is assumed that the present invention is not limited to these modes.

Figure 1:
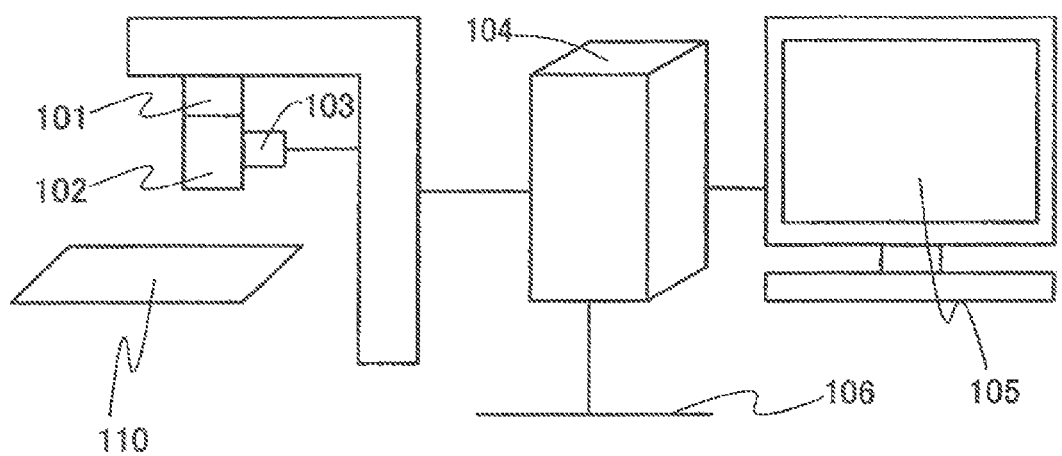
FIG. 1 is a schematic diagram of an, inspection apparatus in one embodiment of the present invention.

FIG. 1 is a schematic diagram showing a configuration of an inspection apparatus in this embodiment mode. An optical lens 102 and coaxial lighting 103 are attached to a digital camera 101, and the digital camera 101 takes an image of an inspection substrate 110. The digital camera 101 takes not a monochrome image but a color image. The taken image is magnified approximately 100 times by the optical lens 102. The taken image is transferred to a computer 104, and image processing is performed in the computer 104. Various kinds of images can be checked on a monitor 105. The computer 104 is connected to another computer through a network 106.

The monitor 105 is used to display the taken image or like so as to be checked visually by an inspector. However, the image processing is performed in the computer 104, so the monitor 105 is only used auxiliarily by the inspector.

Figure 3A:
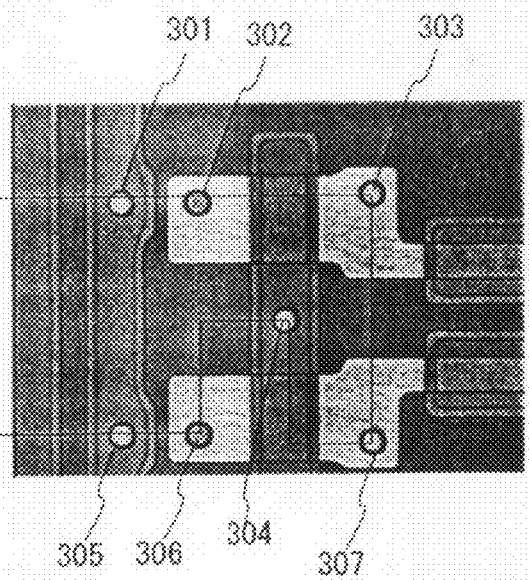
FIGS. 3A to 3C respectively show an color image subjected to image processing in the present invention, a cross-sectional view taken along line A-A' of FIG. 3A, and a magnified view of a lower portion of a contact hole 306.
Figure 3B:
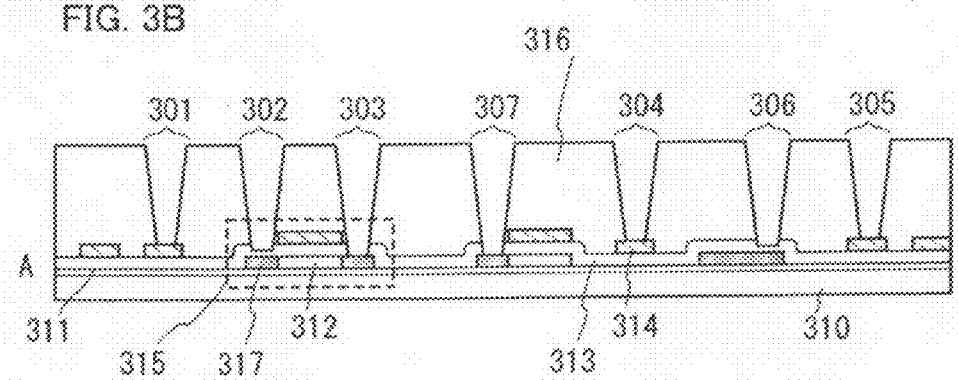

Here, a method for manufacturing a TFT which is an inspection object to obtain a structure shown in FIG. 3B is explained. Note that a method for manufacturing a TFT is not limited to the method for manufacturing a TFT to be described here.

A base film 311 is formed over a substrate 310. As the substrate 310, a substrate which can withstand a processing temperature in a subsequent manufacturing process, such as a glass substrate of, for example, barium borosilicate glass or alumino borosilicate glass, is used. As the base film 311, a silicon nitride oxide film is formed using a plasma CVD method to have a thickness of 10 nm to 400 nm (preferably, 50 nm to 300 nm). Note that the base film 311 may be a single-layer insulating film or a laminated layer of a plurality of insulating films.

Subsequently, a semiconductor film is formed over the base film 311. The semiconductor film is preferably formed without being exposed to the atmosphere after forming the base film 311. A thickness of the semiconductor film is 20 nm to 200 nm (preferably, 40 nm to 170 nm). Note that the semiconductor film may be an amorphous semiconductor, a semi-amorphous semiconductor, or a polycrystalline semiconductor. In addition, silicon germanium as well as silicon can be used for the semiconductor. In the case of using silicon germanium, a concentration of germanium is preferably approximately 0.01 atomic % to 4.5 atomic %.

Note that a crystalline semiconductor film obtained by crystallizing an amorphous semiconductor film is used in this embodiment mode. As a crystallization method, there is a thermal crystallization method using an electrically-heated furnace, a laser crystallization method using laser light, or a lamp annealing crystallization method using infrared light. A crystallization method using a catalytic element can alternatively be used.

Although the semiconductor film is crystallized in this embodiment mode, an amorphous silicon film or a microcrystalline semiconductor film may be directly subjected to a process to be described below without being crystallized. A semiconductor device using an amorphous semiconductor or a microcrystalline semiconductor has the advantage of lower cost and higher yield since it requires fewer manufacturing steps than a semiconductor device using a polycrystalline semiconductor.

In addition, the above-described semi-amorphous semiconductor is a film which includes a semiconductor having an intermediate structure between an amorphous semiconductor and a semiconductor having a crystalline structure (including a single crystal and a polycrystal). This semi-amorphous semiconductor is a semiconductor having a third state which is stable in terms of free energy, and is a crystalline material having short-range order and lattice distortion. The semi-amorphous semiconductor can be dispersed in a non-single crystal semiconductor with a grain size of 0.5 nm to 20 nm.

Subsequently, the semiconductor film is processed to form an island-shaped semiconductor film 312. Then, a gate insulating film 313 is formed to cover the island-shaped semiconductor film 312, and a conductive film 314 to serve as a gate electrode or a wiring of a TFT is formed and patterned over the gate insulating film 313. Using, as a mask, the conductive film 314 or a resist which is formed and processed into a desired shape, the island-shaped semiconductor film 312 is doped with an impurity which imparts n-type conductivity to form an impurity-doped region 317 functioning as a source region, a drain region, an LDD region, and the like. Note that a TFT 315 is formed to be an n-type here, but when the TFT is formed to be a p-type, an impurity which imparts p-type conductivity is added. According to the series of steps above, the TFT 315 can be formed.

Note that after forming the gate insulating film 313, a step of hydrogenating the island-shaped semiconductor film 312 may be performed by performing heat treatment at 300° C. to 450° C. for 1 to 12 hours in an atmosphere containing hydrogen of 3% to 100%. As another hydrogenation method, plasma hydrogenation (using hydrogen excited by plasma) may be performed. According to this hydrogenation step, a dangling bond can be terminated by thermally-excited hydrogen.

Subsequently, an interlayer insulating film 316 is formed to cover the TFT 315. Note that as a material for forming the interlayer insulating film 316, an organic resin film, an inorganic insulating film, an insulating film including a Si—O—Si bond formed using a siloxane-based material as a starting material (hereinafter referred to as a siloxane-based insulating film), or the like can be used. For the siloxane-based insulating film, an organic group containing at least hydrogen (for example, an alkyl group or aromatic hydrocarbon) is used for a substituent. A fluoro group may be used for a substitute. Alternatively, an organic group containing at least hydrogen, and a fluoro group may be used for substituents.

Then, contact holes (301 to 307) are formed in the gate insulating film 313 and the interlayer insulating film 316. Note that the contact holes (301 to 307) can be formed by performing etching using a mask formed from a resist or the like so as to expose the impurity-doped region 317 and can be formed by either wet etching or dry etching. Note that etching may be performed once or separately plural times depending on conditions. When etching is performed plural times, both wet etching and dry etching may be employed.

Through the above steps, the structure shown in FIG. 3B can be obtained. Note that a structure of a TFT to which the inspection method of the invention can be applied is not limited to that shown in FIG. 3B.

The inspection in this embodiment mode means to inspect the structure shown in FIG. 3B and to inspect whether the contact holes (301 to 307) are formed to reach the conductive film 314. The contact holes 301, 303, 304, and 305 are formed to reach the conductive film 314 or the impurity-doped region 317, but the contact holes 302 and 306 are formed without reaching the conductive film 314 or the impurity-doped region 317. In other words, the contact holes 302 and 306 are defects in this manufacturing process. Note that only the contact holes which are formed without reaching the conductive film 314 or the impurity-doped region 317 are described here; however, the case where a contact hole reaches the base film 311 formed below the conductive film 314 (in other words, the case where a contact hole is formed to penetrate the conductive film 314) can also be detected by the inspection method of the invention.

In the inspection method of the invention, such a defect as shown in FIG. 3B can be detected by using a predetermined method to process a color image shown in FIG. 3A.

Note that by using the inspection method of the invention, it can be determined in accordance with a control criterion whether a TFT substrate in which a defect is detected is removed from a manufacturing process or continuously subjected to a subsequent step. In a subsequent step, wirings to be connected to the conductive film 314 through the contact holes are formed.

Note that, by further continuously performing a predetermined step after forming the TFT, various semiconductor devices can be manufactured.

In addition, in the case where a defect can be repaired, even a TFT substrate which is considered as defective by the inspection can be continuously subjected to a subsequent step after being repaired so as to be non-defective.

Subsequently, a contact hole to be inspected in this embodiment mode is explained. In FIGS. 3A and 3B, the contact holes 301, 304, and 305 are contact holes formed to reach the conductive film 314 formed over the base film 311 and the gate insulating film 313 formed over the substrate 310. In this case, when a contact hole is formed to reach the conductive film 314, the contact hole exhibits white. When a contact hole is formed without reaching the conductive film 314, the contact hole exhibits brown due to interference effect by the interlayer insulating film 316. Accordingly, in the case of inspecting this portion, it can be determined whether or not the contact holes 301, 304, and 305 reach the conductive film 314, in other words, whether or not the contact holes are defective, by converting a color space of the color image from an RGB color space into an HSB color space and using saturation (S) among color coordinate components of the obtained HSB color space. This is because the saturation is increased as color of an object becomes vivid and saturation of achromatic color (black, gray, or white) is zero; thus, color depth of the contact hole can be distinguished.

On the other hand, the contact holes 302, 303, 306, and 307 are contact holes formed to reach the impurity-doped region 317 formed over the base film 311 formed over the substrate 310.

In this embodiment mode, it is judged by the color of the contact holes 302, 303, 306, and 307 whether the contact holes 302, 303, 306, and 307 are formed to reach the impurity-doped region 317. The color of a contact hole differs depending on a laminated structure of a film formed below the contact hole. In the case of this embodiment mode, the color appearance of the contact holes differs depending on film color of the impurity-doped region 317 and film color of the gate insulating film 313 formed below the contact holes.

Figure 3C:
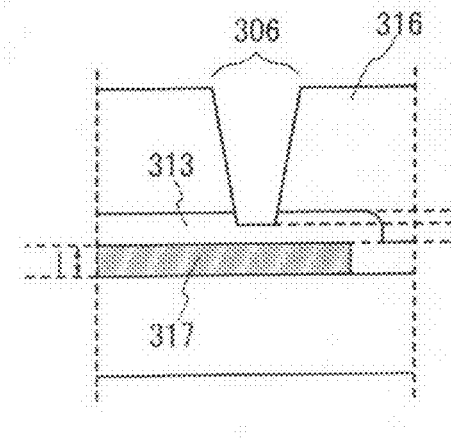

FIG. 3C shows a magnified view in the vicinity of the contact hole 306 of FIG. 3B. As to the semiconductor film in which the impurity-doped region 317 is formed, a film color thereof differs depending on a thickness (l). Specifically, the semiconductor film exhibits pink when the thickness (l) is 66 nm or more; yellow, when 54 nm to less than 66 nm; white, when 30 nm to 50 nm; blue, when 10 nm or less; and black, when less than 10 nm. Therefore, a change in color of a contact hole with a change in thickness of the impurity-doped region 317 in the case of forming the contact hole is utilized. Incidentally, since the semiconductor film is formed to have a thickness of 55 nm in this embodiment mode, the contact hole exhibits yellow. The contact holes 302, 303, 306, and 307 formed with little change in thickness of the semiconductor film exhibit yellow.

In the case of the contact holes 302 and 306 which do not reach the impurity-doped region 317, the thickness (l) of the impurity-doped region 317 is not changed, but a thickness (m') of the gate insulating film 313 is changed compared to a thickness (m) before forming the contact holes and color depth is changed. In other words, the contact hole 306 does not reach the impurity-doped region 317, but is formed to remove part of the gate insulating film 313. In other words, the gate insulating film 313 thinly remains below the contact hole 306, and the thickness (m) is not zero. In such a case, the contact hole 306 exhibits deeper yellow than yellow of the contact holes 303 and 307. The contact hole 302 also exhibits deeper yellow than yellow of the contact holes 303 and 307 since the gate insulating film 313 also remains below the contact hole 302 as is the case with the contact hole 306.

Accordingly, also in the case of inspecting this portion, it can be determined, whether or not the contact hole is defective, by converting a color space of the color image from an RGB color space into an HSB color space, and using saturation (S) among color coordinate components of the obtained HSB color space.

The gate insulating film 303 remains as below the contact holes 302 and 306 due to defective etching. When the gate insulating film 313 remains as described above, electrical connection cannot be obtained even when a wiring is formed in a subsequent TFT manufacturing process, and a defect is caused. Therefore, it is necessary to perform an inspection after forming the contact hole to determine whether the gate insulating film 313 in a portion of the contact hole is removed by etching. By using the inspection method of the invention, it can be judged whether the gate insulating film 313 is removed by etching, and manufacturing process conditions can be determined by using an inspection result as data for judging manufacturing process conditions. Therefore, product quality can be improved.

Figure 2:
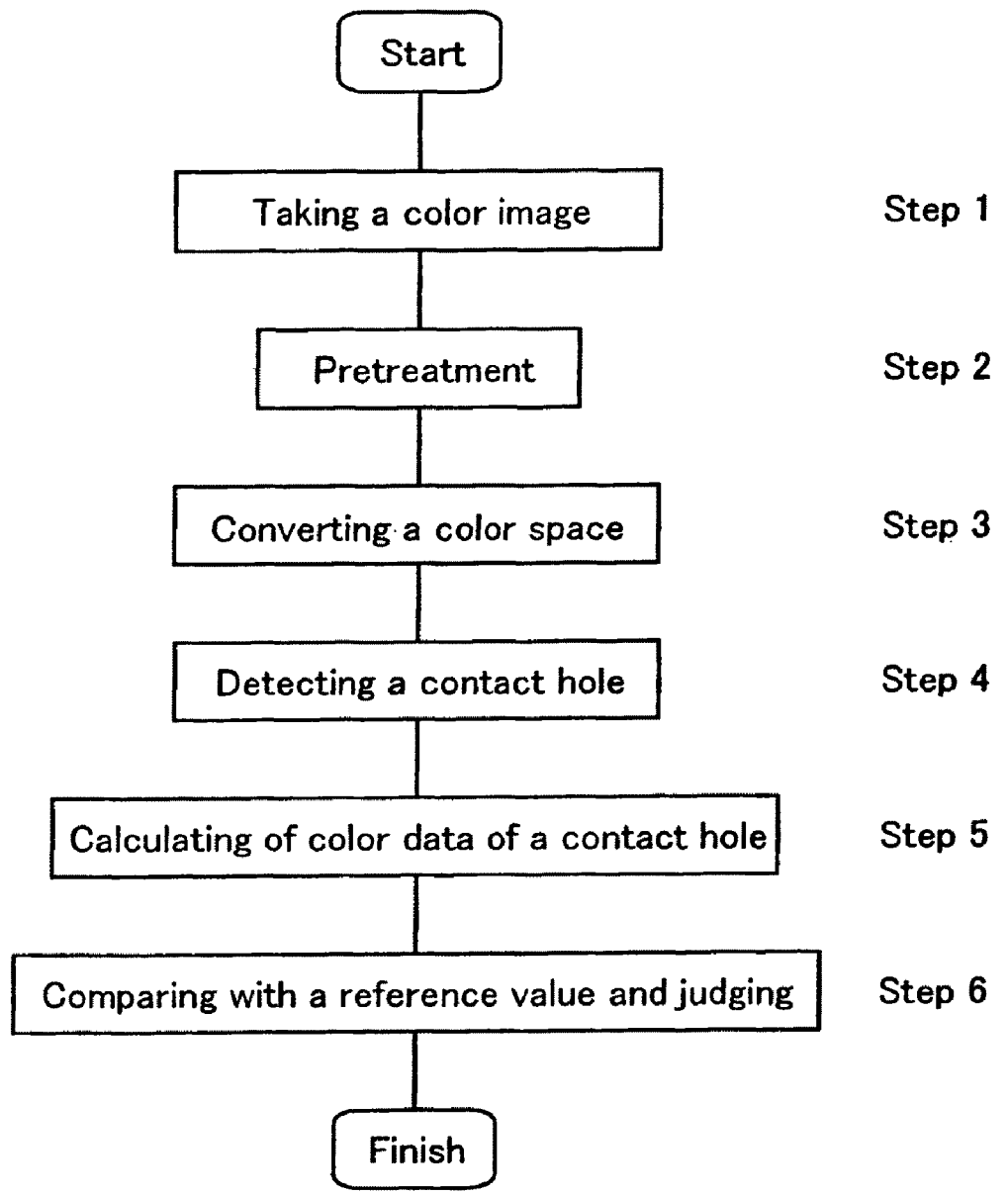
FIG. 2 is a flow chart showing an operation procedure of an inspection method in the present invention.

Hereinafter, a specific technique for the inspection method in this embodiment mode is explained. FIG. 2 is a flow chart showing steps of detecting defective etching of a contact hole.

First, an inspection substrate is irradiated with the coaxial lighting 103, and an optical microscope image of an inspection region over the inspection substrate is taken with the digital camera 101 and the optical lens 102 (Step 1). In this embodiment mode, FIG. 3A is used as a color image which is taken in Step 1. As described above, the contact holes 301, 303, 304, 305, and 307 are normally-etched contact holes, and exhibit white or yellow as deep as silicon therearound. The contact holes 302 and 306 are contact holes in which the gate insulating film 313 is not completely removed due to defective etching and defective opening is caused, and exhibit deeper yellow than silicon therearound. It is an object of this embodiment mode to judge the contact holes 302 and 306 to be defective by examining color data of each contact hole after detecting all contact holes in the image.

Pretreatment such as noise removal is performed on the color image (Step 2).

The color image includes color coordinate components of an RGB color space, which is converted into an HSB color space including three color coordinate components, a hue (H), saturation (S), and brightness (B) (Step 3). Each color coordinate component of the HSB color space, which is obtained by conversion, is stored in a memory. Since the HSB color space is a color space adjusted to a tendency for human to sense color with the naked eye, the HSB color space is more suitable than the RGB color space for human to interpret color of the image. For example, if brightness (B) is used, it can be judged whether an object is bright, and if saturation (S) is used, it can be judged whether color of an object is vivid. It is difficult to make these judgments only with the RGB color space.

Figure 4A:
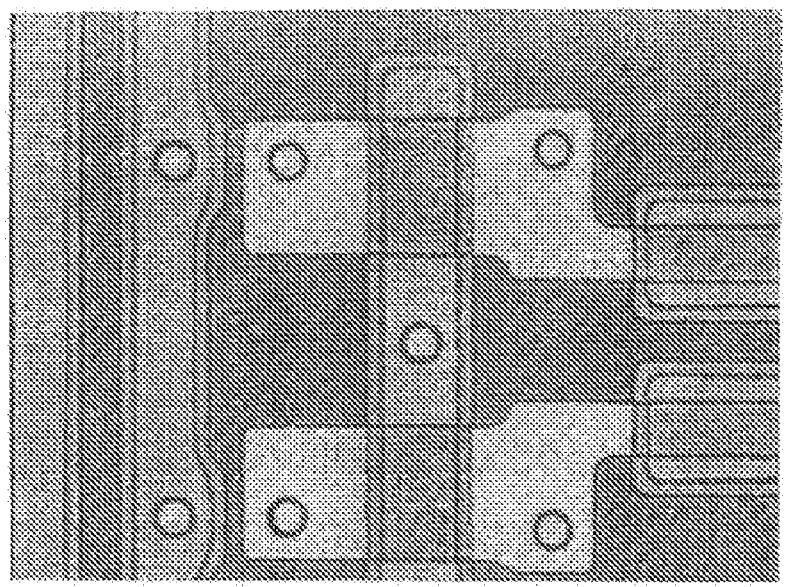
FIGS. 4A and 4B show a gray-scale image and a binary image in the present invention.
Figure 5:
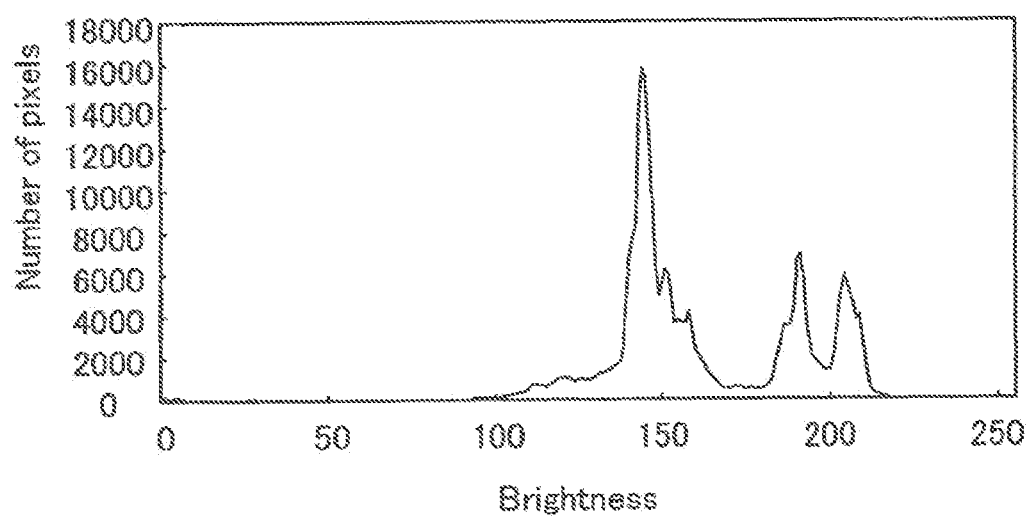
FIG. 5 is a histogram of a gray-scale image in the present invention.

Subsequently, all contact holes (the contact holes 301 to 307) in the color image are detected (Step 4). In order to do so, brightness (B) among the color coordinate components of the HSB color space is used to generate a gray-scale image expressed by the value of brightness. The generated gay-scale image is shown in FIG. 4A. In addition, a histogram representing the number of pixels to brightness of the gray-scale image is FIG. 5. Since the brightness is high when it is bright and is low when it is dark, brightness of the contact holes 301, 303, 304, 305, and 307 which exhibit yellow in the color image and that of the contact holes 302 and 306 which exhibit white is high. Brightness is uniformly low in a dark portion around each contact hole. Thus, it is suitable to use brightness in detecting all contact holes in the image regardless of whether or not the contact holes are defective. Therefore, brightness is used in this embodiment mode to generate the gray-scale image. However, a color coordinate component in generating the gray-scale image does not necessarily need to be brightness, and may be appropriately selected depending on an inspection object.

Figure 4B:
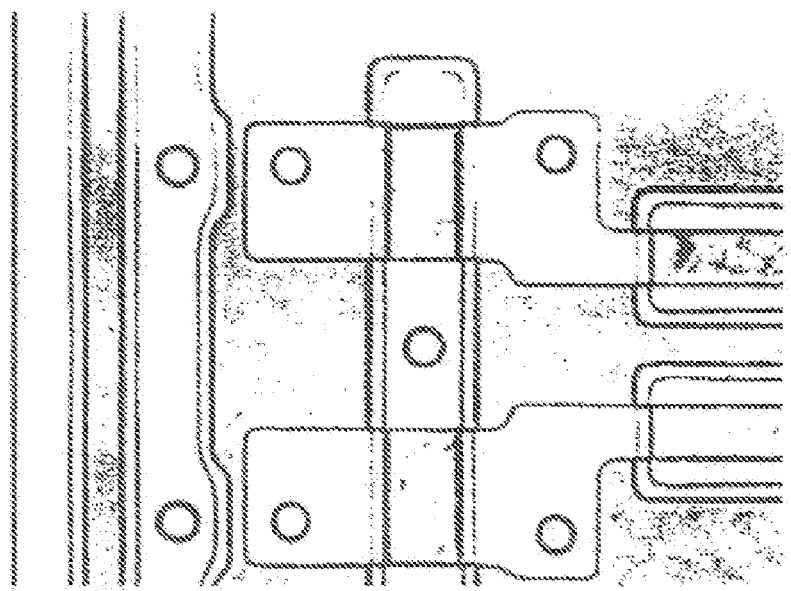

Subsequently, a binary image is generated from the generated gray-scale image. Various techniques can be used to generate the binary image from the gray-scale image, but in this embodiment mode, a threshold is determined by a p-tile method to generate the binary image. The p-tile method is a method in which a value where a proportion of white pixels to entire pixels in the binary image becomes p is regarded as a threshold using a histogram. In this embodiment mode, it is found by preliminary analysis of a similar image that p is preferably 0.15. Thus, the p-tile method is performed with p=0.15. Consequently, the threshold is calculated to be 140. The gray-scale image is binarized considering a pixel having a brightness of less than 140 as black and a pixel having brightness of 140 or more as white to generate the binary image. The generated binary image is shown in FIG. 4B. All contact holes (the contact holes 301 to 307) become white connected regions in the binary image. Here, the connected region means a cluster of connected white pixels in the binary image. Since brightness is small in a dark portion around each contact hole, the dark portion becomes black in the binary image and functions to separate the contact hole from the peripheral connected region. Thus, all contact holes are connected regions in the binary image.

Subsequently, all connected regions in the binary image are detected by labeling, and coordinate data of each pixel occupied by each connected region is stored in a memory. As for each detected connected region, a characteristic amount with which characteristics of the contact hole can be captured is calculated to sort out only a connected region corresponding to the contact hole. As the characteristic amount, an area, a boundary length, degree of circularity, center of gravity, or the like can be given. In this embodiment mode, an area and degree of circularity are used as the characteristic amount.

First, among the connected regions, only connected regions each having an area close to that of the contact hole are selected. Here, the area is the number of pixels in the connected region. In this embodiment mode, only connected regions each having an area of 400 to 700 are selected.

Subsequently, as for each connected region selected in the preceding paragraph, degree of circularity is calculated to further sort out a connected region having degree of circularity close to 1. Here, the degree of circularity is an amount defined by $4\pi S/l^2$ (S: area, l: boundary length) and becomes 1 in the case of a complete circle.

The above processing makes it possible to detect all contact holes (contact holes 301 to 307) in the taken image and to obtain coordinate data of each pixel occupied by each contact hole. Note that the degree of circularity of the connected region is calculated in this embodiment mode because the contact hole is circular. If an inspection object is not circular, a method for capturing characteristics of the connected region may be changed in accordance with the shape. In addition, coordinate data of an inspection object may be obtained using a technique such as pattern matching.

Subsequently, color data of each contact hole detected by the above processing is examined (Step 5). In this embodiment mode, as for each of all contact holes (contact holes 301 to 307) detected by the processing to the preceding paragraph, a mean value per pixel of saturation (S) of the pixel occupied by the contact hole is calculated. For the calculation of the mean value of saturation, saturation (S) among the color coordinate components of the HSB color space is used. As described above, the saturation is increased as color becomes more vivid and saturation of achromatic color (black, gray, or white) is zero; therefore, the saturation is suitable for examining whether color of the object is vivid. Since it can be judged, whether or not contact hole opening is defective, if vividness of a contact hole is examined, saturation is used as the color coordinate component in this embodiment mode. However, it may be determined which color coordinate component is used to judge whether or not contact hole opening is defective.

Lastly, the mean value of saturation (S) per pixel in each contact hole is compared with a preset reference value. If the mean value of saturation is smaller than the reference value, contact hole opening is judged as not defective, and if larger, the contact hole opening is judged as defective (Step 6). Here, it is assumed that the preset reference value is 190. A judgment result is shown in FIG. 6. The contact holes 302 and 306 where defective etching has occurred are judged as defective, and the contact holes 301, 303, 304, 305, and 307 where defective etching has not occurred are judged as not defective. In other words, it can be judged that in the contact holes 302 and 306, the gate insulating film 313 is not completely removed and defective contact hole opening has occurred. Note that electrical connection cannot be obtained in the contact holes 302 and 306 which are defective in opening even when the process is continued and a wiring is formed in a subsequent step, which results in a defective substrate.

In this embodiment mode, this result can be transmitted to another computer through a network 106, and manufacturing process conditions can be determined by using the judgment result as data for judging the manufacturing process conditions. Accordingly, product quality can be improved.

As described above, in the case of using the pattern inspection method of the invention, a color image of an inspection object is taken first, and a color space is converted from an RGB color space into an HSB color space. Then, defective etching of a contact hole is inspected by using two color coordinate components that are brightness (B) and saturation (S) among color information of the HSB color space which is obtained by the conversion. Such an inspection cannot be conducted by image processing of a monochrome image, and becomes possible by using a color image.

This embodiment mode is explained using a contact hole as an example. However, the inspection method of the invention can be applied to an inspection object having an uneven surface such as a columnar spacer or a reflecting electrode having a complex cross-sectional shape.

As described above, an appearance inspection which has been difficult to be automated can be automated by using the pattern inspection method of the invention. Note that the case of applying the inspection method of the invention to a manufacturing process of a TFT is described in this embodiment mode. However, the invention is not limited thereto and can be applied to manufacturing of all semiconductor devices (a liquid crystal display device, an electroluminescent display, a plasma display, an integrated circuit, and the like).

Further, a color image is used in the invention; therefore, a more subtle difference among inspection objects than ever before can be detected. In addition, in the invention, a judgment result of inspection can be transmitted to another computer through a network, and manufacturing process conditions can be determined by using the judgment result as data for judging the manufacturing process conditions. Accordingly, product quality can be improved.

Embodiment 1

This embodiment describes examples of electronic appliances with a TFT inspected by an inspection method and/or an inspection apparatus of the present invention. As the electronic appliances, a camera such as a video camera or a digital camera, a goggle type display (head mounted display), a navigation system, a sound reproduction device (such as a car audio component), a notebook personal computer, a game machine, a mobile information terminal (such as a mobile computer, a cellular phone, a mobile game machine, or an electronic book), an image reproduction device equipped with a recording medium (specifically, a device which reproduces a recording medium such as a digital versatile disc (DVD) and is equipped with a display for displaying the image), and the like are given. FIGS. 7A to 7E show the specific examples of these electronic appliances.

Figure 7A:
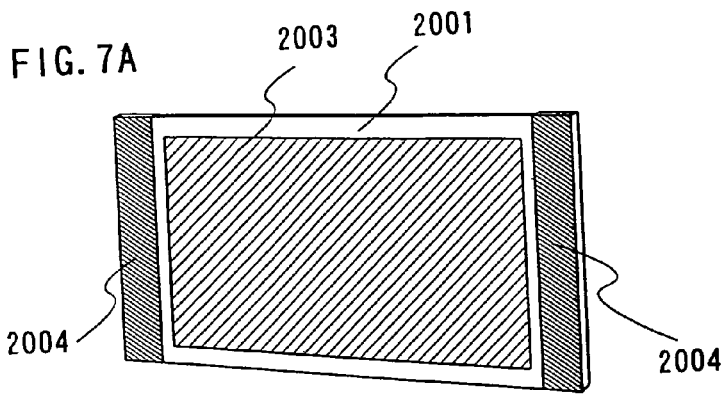
FIGS. 7A to 7E show examples of electronic appliances to which the present invention is applied.

FIG. 7A shows a display device which corresponds to, for example, a television receiving device. The display device includes a case 2001, a display portion 2003, speaker portions 2004, and the like. The display device in which the operating characteristic of a TFT is enhanced can be manufactured when the display device is inspected by an inspection method and/or an inspection apparatus of the present invention since a TFT without defective etching of a contact hole can be manufactured.

Figure 7B:
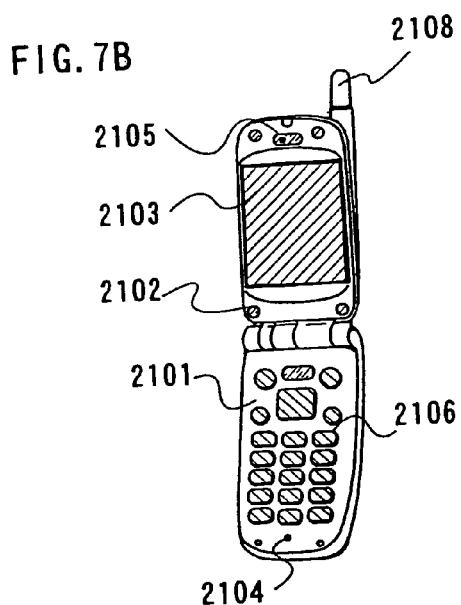

FIG. 7B shows a cellular phone, including a main body 2101, a case 2102, a display portion 2103, an audio input portion 2104, an audio output portion 2105, operation keys 2106, an antenna 2108, and the like. The cellular phone in which the operating characteristic of a TFT is enhanced can be manufactured when a substrate having the TFT included in the cellular phone is inspected by an inspection method and/or an inspection apparatus of the present invention since a TFT without defective etching of a contact hole can be manufactured.

Figure 7C:
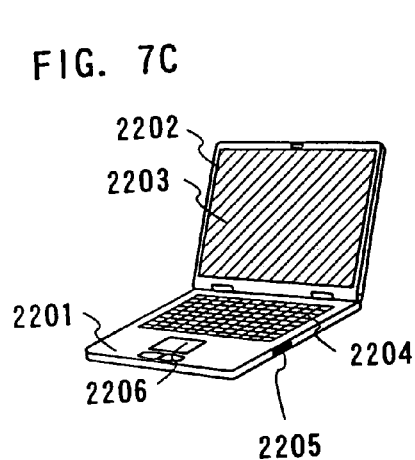

FIG. 7C shows a notebook personal computer, including a main body 2201, a case 2202, a display portion 2203, a keyboard 2204, an external connection port 2205, a pointing mouse 2206, and the like. The notebook personal computer in which the operating characteristic of a TFT is enhanced can be manufactured when a substrate having the TFT included in the notebook personal computer is inspected by an inspection method and/or an inspection apparatus of the present invention since a TFT without defective etching of a contact hole can be manufactured.

Figure 7D:
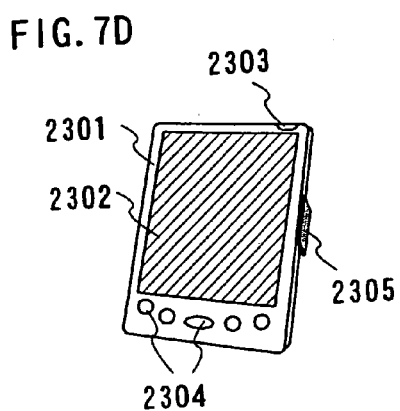

FIG. 7D shows a mobile computer, including a main body 2301, a display portion 2302, a switch 2303, operation keys 2304, an infrared port 2305, and the like. The mobile computer in which the operating characteristic of a TFT is enhanced can be manufactured when a substrate having the TFT included in the mobile computer is inspected by an inspection method and/or an inspection apparatus of the present invention since a TFT without defective etching of a contact hole can be manufactured.

Figure 7E:
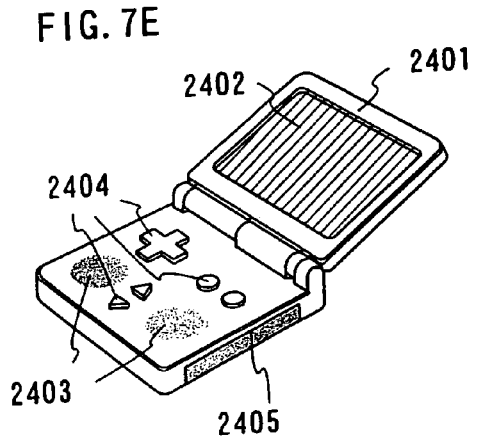

FIG. 7E shows a mobile game machine, including a case 2401, a display portion 2402, speaker portions 2403, operation keys 2404, a recording medium inserting portion 2405, and the like. The mobile game machine in which the operating characteristic of a TFT is enhanced can be manufactured when a substrate having the TFT included in the mobile game machine is inspected by an inspection method and/or an inspection apparatus of the present invention since a TFT without defective etching of a contact hole can be manufactured.

As discussed above, the applicable range of the present invention is so wide that the present invention can be applied to electronic appliances of various fields. In addition, the electronic appliances of this embodiment can be freely combined with the embodiment.

This application is based on Japanese Patent Application serial No. 2005-018004 filed in Japan Patent Office on Jan. 26, 2005, the entire contents of which are hereby incorporated by reference.

What is claimed is:

1. A pattern inspection apparatus comprising:
    means for magnifying and taking a color image including a plurality of pixels, wherein the color image includes a contact hole over a substrate, and the contact hole overlaps at least two of the plurality of pixels;
    a generator for generating a first color information of each of the plurality of pixels, wherein the first color information includes three color coordinate components, red (R), green (G), and blue (B), of an RGB color space;
    a converter for converting the first color information of each of the plurality of pixels into a second color information including first, second and third color coordinate components;
    a generator for generating a gray-scale image in accordance with the first color coordinate component;
    a generator for generating a binary image from the gray-scale image by regarding one of the plurality of pixels having the first color coordinate component of less than a predetermined threshold as black pixel and another one of the plurality of pixels having the first color coordinate component of more than the predetermined threshold as a white pixel;
    means for detecting the contact hole from the binary image to obtain coordinate data of at least two of the plurality of pixels overlapped by the contact hole;
    means for calculating a mean value of the second color coordinate component of at least two of the plurality of pixels overlapped by the contact hole; and
    means for comparing the mean value of the second color coordinate component in each contact hole with preset non-defective reference color information, and judging the contact hole.

2. A pattern inspection apparatus according to claim 1, wherein a data of the color image is generated using a digital camera attached to an optical microscope or a laser microscope.

3. A pattern inspection apparatus comprising:
    means for magnifying and taking a color image including a plurality of pixels, wherein the color image includes a contact hole over a substrate, and the contact hole overlaps at least two of the plurality of pixels;
    means for generating a first color information of each of the plurality of pixels, wherein the first color information includes three color coordinate components, red (R), green (G), and blue (B), of an RGB color space;
    means for converting the first color information of each of the plurality of pixels into a second color information including three color coordinate components, hue (H), saturation (S), and brightness (B) of an HSB color space;
    means for generating a gray-scale image in accordance with the brightness (B);
    a generator for generating a binary image from the gray-scale image by regarding one of the plurality of pixels having a brightness (B) of less than a predetermined threshold as black pixel and another one of the plurality of pixels having a brightness (B) of more than the predetermined threshold as a white pixel;
    means for detecting the contact hole from the binary image to obtain coordinate data of at least two of the plurality of pixels overlapped by the contact hole;
    means for calculating a mean value of the saturation (S) of at least two of the plurality of pixels overlapped by the contact hole; and
    means for judging the contact hole by comparing the mean value of the saturation (S) in the contact hole with a preset saturation (S) of a non-defective contact hole.

4. A pattern inspection apparatus according to claims 3, wherein a data of the color image is generated using a digital camera attached to an optical microscope or a laser microscope.

5. A pattern inspection apparatus comprising:
    means for magnifying and taking a color image including a plurality of pixels, wherein the color image includes a contact hole over a substrate, and the contact hole overlaps at least two of the plurality of pixels;
    means for generating a first color information of each of the plurality of pixels, wherein the first color information includes three color coordinate components, red (R), green (G), and blue (B), of an RGB color space;
    means for converting the first color information of each of the plurality of pixels into a second color information including three color coordinate components, hue (H), saturation (S), and brightness (B) of an HSB color space;
    means for taking brightness (B) which is suitable to specify a position of the contact hole from the second color information;
    means for specifying the position of the contact hole based on a characteristic amount of an image obtained using the brightness (B);
    means for taking a saturation (S) which is previously selected and is suitable to judge the contact hole from the second color information; and
    means for judging the contact hole by comparing a reference saturation (S) of preset non-defective reference color information with the saturation (S).

6. A pattern inspection apparatus according to claim 5, wherein a data of the color image is generated using a digital camera attached to an optical microscope or a laser microscope.

* * * * *